United States Patent
Xu

(10) Patent No.: US 10,167,275 B2
(45) Date of Patent: Jan. 1, 2019

(54) AZD9291 INTERMEDIATE AND PREPARATION METHOD THEREFOR

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 15/822,060

(22) Filed: Nov. 24, 2017

(65) Prior Publication Data

US 2018/0072706 A1    Mar. 15, 2018

Related U.S. Application Data

(63) Continuation of application No. PCT/CN2016/081941, filed on May 13, 2016.

(30) Foreign Application Priority Data

Jun. 16, 2015 (CN) .......................... 2015 1 0332787

(51) Int. Cl.
    C07D 403/04    (2006.01)
    C07C 277/08    (2006.01)
    C07C 279/18    (2006.01)
(52) U.S. Cl.
    CPC .......... *C07D 403/04* (2013.01); *C07C 277/08* (2013.01); *C07C 279/18* (2013.01)

(58) Field of Classification Search
    CPC ... C07C 277/08; C07C 279/08; C07C 403/04; C07D 403/04
    See application file for complete search history.

(56) References Cited

U.S. PATENT DOCUMENTS

2001/0056123 A1    12/2001    Nakagawa et al.

FOREIGN PATENT DOCUMENTS

| CN | 104910049 A | 9/2015 |
| WO | 2013014448 A1 | 1/2013 |

*Primary Examiner* — Deepak R Rao
(74) *Attorney, Agent, or Firm* — Perkins Coie LLP

(57) ABSTRACT

Disclosed are an intermediate, N-[2-[[2-(dimethylamino)ethyl]methylamino]-4-methoxy-5-formamidine]phenyl-2-propenamide (II), applicable in preparing AZD9291 (I) and a preparation method for the intermediate. Preparation steps of the preparation method comprise: 2-fluoro-4-methoxyaniline, serving as a starting material, undergoes amidation, substitution, nitrification, reduction and guanidination reactions to prepare N-[2-[[2-(dimethylamino)ethyl]methylamino]-4-methoxy-5-formamidine]phenyl-2-propenamide (II). Also disclosed is a method for preparing AZD9291 (I) by means of a cyclization reaction between the compound of a formula II and (2E)-3-dimethylamino-1-(1-methyl-1H-indol-3-yl)-2-propen-1-one (III). The preparation method has readily available raw materials and a simple process and is economical, environmentally friendly, and suitable for industrialized production.

8 Claims, No Drawings

AZD9291 INTERMEDIATE AND PREPARATION METHOD THEREFOR

CROSS REFERENCE TO RELATED APPLICATIONS

This application is a continuation of PCT/CN2016/081941 filed 2016 May 13, which claims priority to CN 201510332787.6 filed 2015 Jun. 16, both of which are incorporated herein by reference.

TECHNICAL FIELD

The invention belongs to the technical field of organic synthetic route design and preparation of a crude drug and an intermediate therefor, and particularly relates to a preparation method for AZD9291 as a drug which is possibly used for treating a non-small cell lung cancer (NSCLC).

BACKGROUND ART

AZD9291 is a third-generation irreversible epidermal growth factor receptor tyrosine kinase inhibitor which is developed by the AstraZeneca UK Company. and can be used for activating resistance-mutated EGFR. AZD9291 was granted as a 'breakthrough therapy drug' by Food and Drug Administration (FDA) in April 2014, the drug is an oral drug, and is improved for overcoming shortcomings of a first-generation EGFR targeted drug, and therefore, the side effects such as diarrhea and skin rash are fewer than the side effects of the first-generation EGFR targeted drug. According to the annual meeting report of American Society of Clinical Oncology (ASCO) in 2014, the curative effect of AZD9291 for treating T790M mutation people whose diseases were progressed after those people were treated by the first-generation EGFR targeted drug was 66%. The total disease control rate of mutation positive patients treated with AZD9291 was 94%.

The chemical name of AZD9291 is N-{2-[[2-(dimethylamino)ethyl]methylamino]-4-methoxy-5-[[4-(1-methyl-1H-indol-3-yl)-2-pyrimidyl]amino]phenyl}-2-propenamide, and a structural formula of AZD9291 is:

AZD9291

International patent WO2013014448 has reported a synthetic method of AZD9291, and preparation steps of the synthetic method comprise coupling on an indole derivative and dichloropyrimidine, substitution on the indole derivative and a phenylamine derivative, condensation on a fluoride parent ring and substituted ethylenediamine, reduction of nitro, amidation, reduction and dehydrogenation and the like to prepare AZD9291 (I).

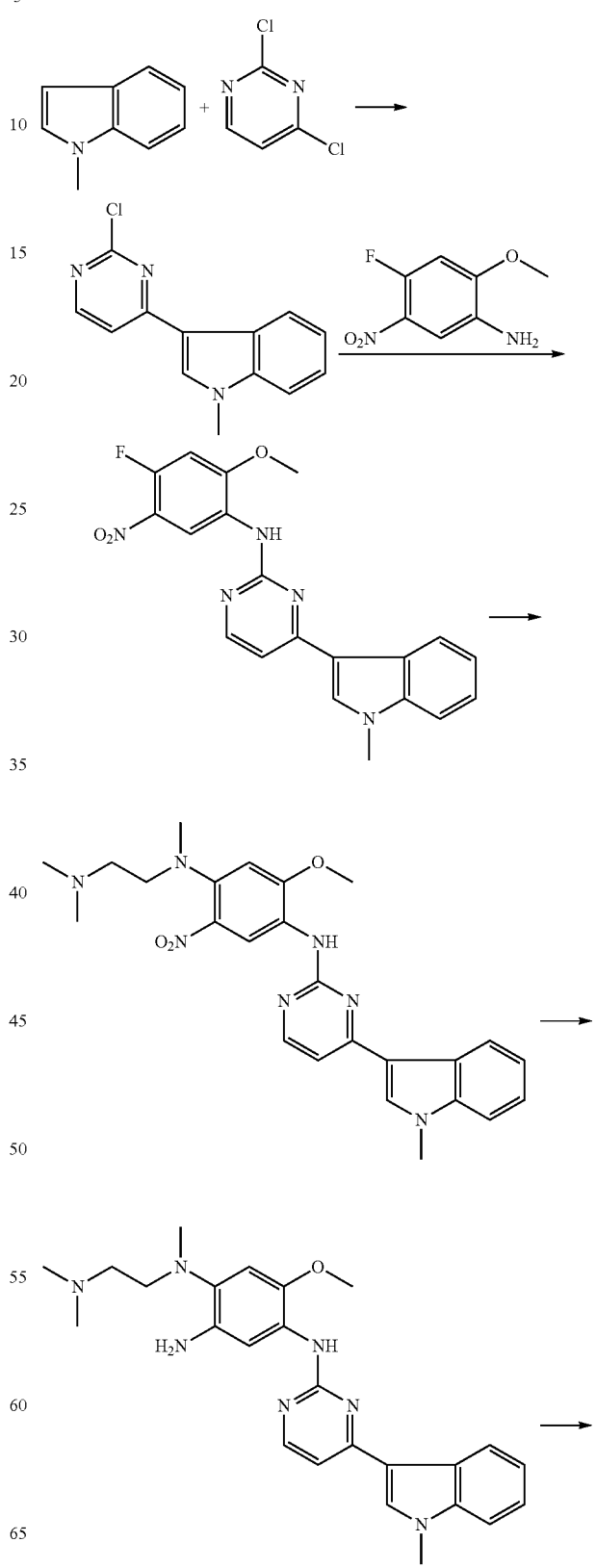

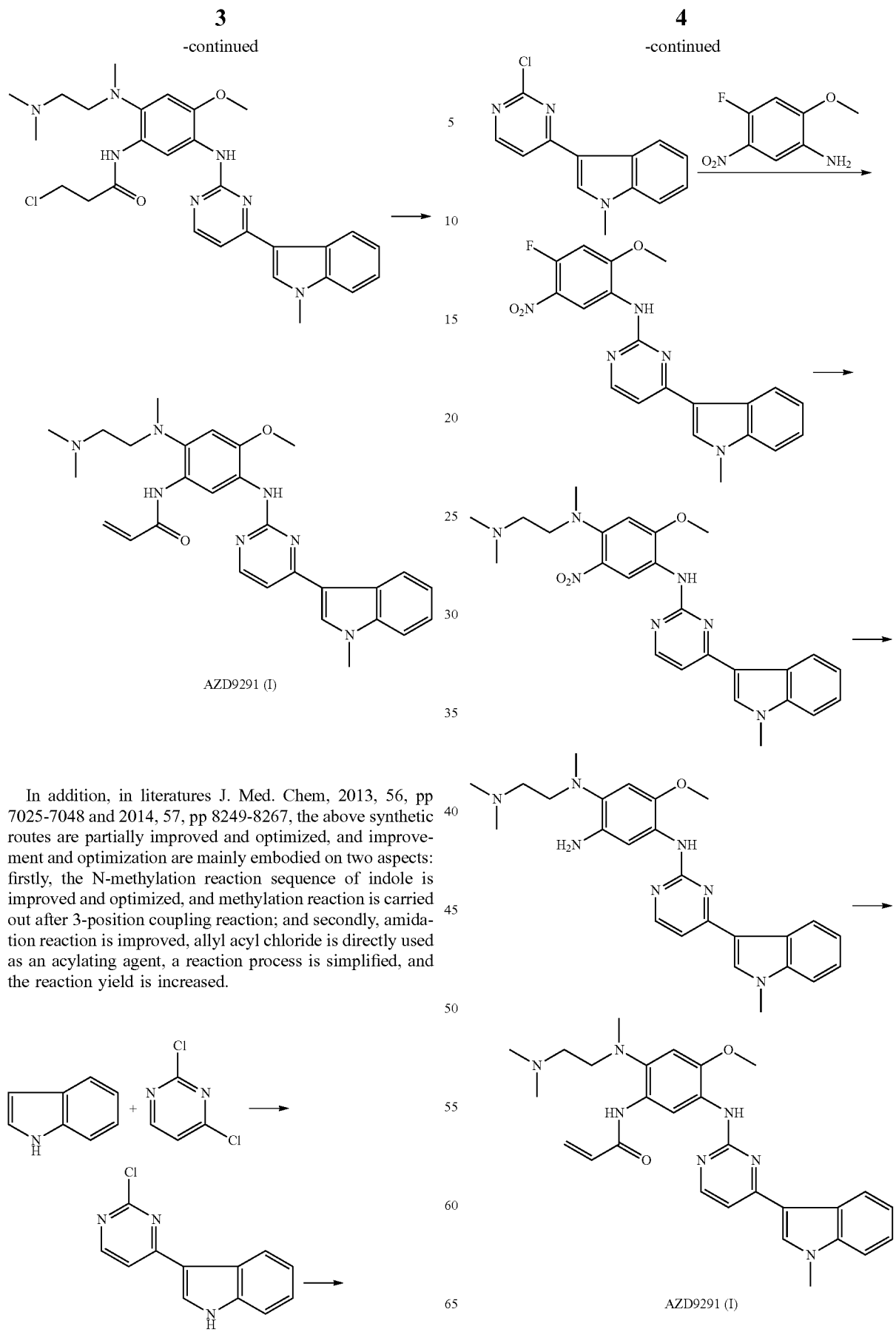

In addition, in literatures J. Med. Chem, 2013, 56, pp 7025-7048 and 2014, 57, pp 8249-8267, the above synthetic routes are partially improved and optimized, and improvement and optimization are mainly embodied on two aspects: firstly, the N-methylation reaction sequence of indole is improved and optimized, and methylation reaction is carried out after 3-position coupling reaction; and secondly, amidation reaction is improved, allyl acyl chloride is directly used as an acylating agent, a reaction process is simplified, and the reaction yield is increased.

According to analysis on the disclosed preparation method for AZD9291, in the basic thinking, pyrimidine rings are successively connected through 3-position coupling for forming an indole ring, and then through reactions such as substitution, reduction and amidation on the pyrimidine rings successively, functional-group transformation of a side chain is realized, and therefore, a target compound is prepared. These methods have the shortcomings of rare raw materials, more steps, higher cost and the like. Although reactions such as N-methylation and amidation of indole were optimized in literature report, only local reactions are optimized, in the core reaction route, preparation is realized by step-by-step accumulation of functional groups of a starting material, and obviously, the synthesis idea does not conform to the concept about atom economy in the modern green chemistry.

For overcoming existing process defects, a preparation technology which is simple in process, economical and environmentally friendly, and high in quality is developed, and particularly, a process technology capable of adapting to industrial production needs to be sought, and is of great realistic significance on improvement of the economic and social benefits of the drug.

SUMMARY OF THE INVENTION

The invention aims to provide an AZD9291 (I) preparation method which has the advantages of accessible raw materials, simple process and high economy and environmental friendliness, and is suitable for industrial production.

In order to achieve the above objective, a compound N-[2-[[2-(dimethylamino)ethyl]methylamino]-4-methoxy-5-formamidine]phenyl-2-propenamide as shown in a formula II is designed and prepared in the invention,

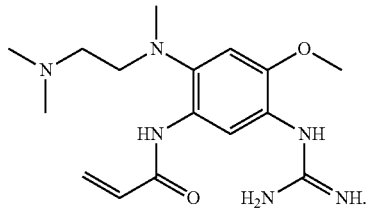

A preparation method of the compound N-[2-[[2-(dimethylamino)ethyl]methylamino]-4-methoxy-5-formamidine]phenyl-2-propenamide comprises the following steps: carrying out amidation reaction on 2-fluoro-4-methoxyphenylamine (IV) and acryloyl chloride in the presence of an acid-binding agent to prepare N-(2-fluoro-4-methoxy)phenyl-2-propenamide (V), carrying out substitution reaction on the prepared N-(2-fluoro-4-methoxy)phenyl-2-propenamide (V) and $N^1,N^1,N^2$-trimethyl-1,2-ethylenediamine under the effect of an alkali accelerator to prepare N-[2-[[2-(dimethylamino)ethyl]methylamino]-4-methoxy phenyl-2-propenamide (VI), carrying out nitrification reaction on the prepared N-[2-[[2-(dimethylamino)ethyl]methylamino]-4-methoxy]]phenyl-2-propenamide (VI) to prepare N-[2-[[2-(dimethylamino)ethyl]methylamino]-4-methoxy-5-nitro]phenyl-2-propenamide (VII), carrying out nitro reduction reaction on the prepared N-[2-[[2-(dimethylamino)ethyl]methylamino]-4-methoxy-5-nitro]phenyl-2-propenamide VII to prepare N-[2-[[2-(dimethylamino)ethyl]methylamino]-4-methoxy-5-amino]phenyl-2-propenamide (VIII), and carrying out guanidination reaction on the prepared N-[2-[[2-(dimethylamino)ethyl]methylamino]-4-methoxy-5-amino]phenyl-2-propenamide (VIII) to prepare N-[2-[[2-(dimethylamino)ethyl]methylamino]-4-methoxy-5-formamidine]phenyl-2-propenamide (II).

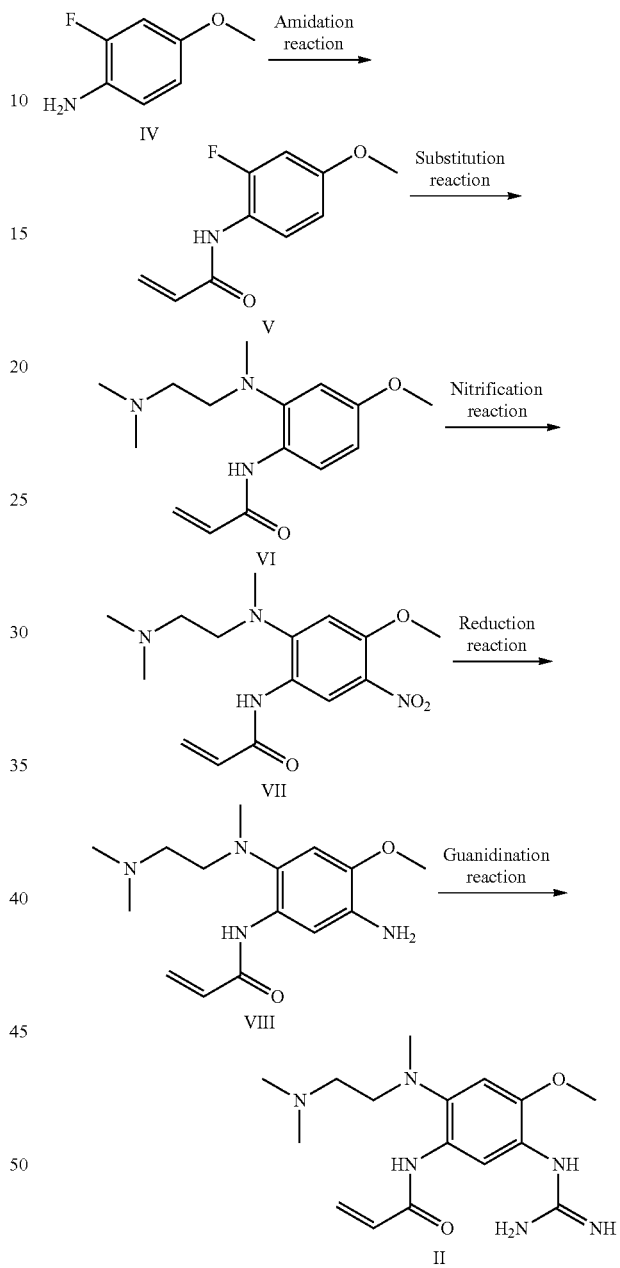

The acid-binding agent for the amidation reaction is triethylamine, sodium bicarbonate, potassium carbonate, lithium carbonate, cesium carbonate, potassium tert-butoxide or sodium tert-butoxide, and is triethylamine or potassium carbonate preferably.

A temperature of the amidation reaction is −25° C. to 25° C., and is 0-25° C. preferably; and a solvent is dichloromethane, 1,2-dichloroethane, acetonitrile, methylbenzene, tetrahydrofuran, dimethyl carbonate or dioxane, and is dichloromethane or tetrahydrofuran preferably.

The alkali accelerator for the substitution reaction is triethylamine, pyridine, N-methylmorpholine, diisopropylethylamine, 4-dimethylaminopyridine, triethylene diamine, 1,8-diazabicycloundec-7-ene or tetramethylethylenediamine, and is diisopropylethylamine or tetramethylethylenediamine preferably.

A temperature of the substitution reaction is 85-95° C.

A solvent for the substitution reaction is N,N-dimethylformamide or N,N-dimethylacetamide.

A nitrating agent for the nitrification reaction is nitric acid or potassium nitrate.

A reducing agent for the nitro reduction reaction is iron, zinc, magnesium, sodium hydrosulfite, hydrazine hydrate or hydrogen.

When the reducing agent for the nitro reduction reaction is hydrazine hydrate, ferric trichloride and activated carbon are used as catalysts.

When the reducing agent for the nitro reduction reaction is hydrogen, palladium/carbon, palladium/carbon hydroxide or raney nickel is used as a catalyst.

A guanidination agent for the guanidination reaction is hydrogen cyanamide.

A temperature of the guanidination reaction is 85-95° C., and a solvent is n-butanol.

The invention further provides a method for preparing AZD9291 (I) by using an intermediate N-[2-[[2-(dimethylamino)ethyl]methylamino]-4-methoxy-5-formamidine]phenyl-2-propenamide (II) and (2E)-3-dimethylamino-1-(1-methyl-1H-indole-3-yl)-2-propen-1-one (III).

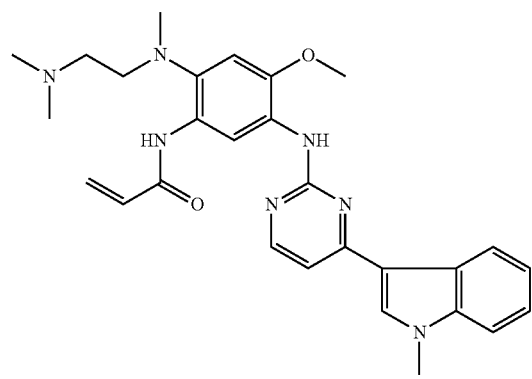

AZD9291 (I)

Preparation steps of the method include: the N-[2-[[2-(dimethylamino)ethyl]methylamino]-4-methoxy-5-formamidine]phenyl-2-propenamide (II) and the (2E)-3-dimethylamino-1-(1-methyl-1H-indole-3-yl)-2-propen-1-one (III) are subjected to cyclization reaction under the effect of a catalyst to prepare AZD9291 (I).

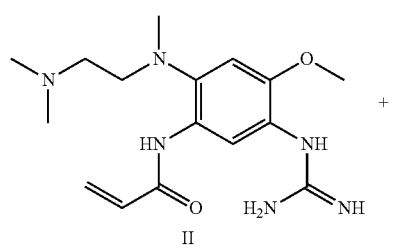

II

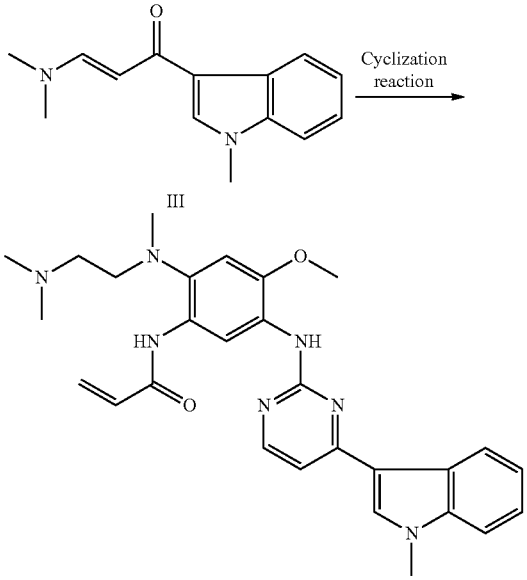

AZD9291 (I)

A molar ratio of raw materials including the N-[2-[[2-(dimethylamino)ethyl]methylamino]-4-methoxy-5-formamidine]phenyl-2-propenamide (II) and the (2E)-3-dimethylamino-1-(1-methyl-1H-indole-3-yl)-2-propen-1-one (III) for the cyclization reaction is 1:0.5-1.5, and is 1:1.1-1.3 preferably.

The catalyst for the cyclization reaction is sodium hydride, potassium hydride, sodium hydroxide, potassium hydroxide, sodium tert-butoxide, potassium tert-butoxide, sodium methoxide, sodium ethoxide, sodium carbonate, potassium carbonate or cesium carbonate, and is sodium hydroxide or sodium methoxide preferably.

A temperature of the cyclization reaction is 50-150° C., and is 95-105° C. preferably.

A solvent for the cyclization reaction is methylbenzene, dimethylbenzene, N,N-dimethylformamide, N,N-dimethylacetamide, n-butanol, isobutanol or tert-butyl alcohol, and is N,N-dimethylformamide or n-butanol preferably.

Compared with the prior art, the preparation method for AZD9291 (I) involved in the invention has the characteristics of accessible raw materials, simple process, high economy and environmental friendliness, and the like, therefore, industrial production of the crude drug is facilitated, and development of the economic technology is promoted.

DETAILED DESCRIPTION OF THE INVENTION

The technical solution of the invention will be further described in detail in a non-limiting manner with reference to several preferred examples below. Preparation of the raw material 2-fluoro-4-methoxyphenylamine (IV) can refer to preparation for the same compound in the literature Bioorganic & Medicinal Chemistry Letters, 20(12), 3526-3529; 2010 or Synthesis, (11), 1599-1603; 1998; and preparation of the raw material (2E)-3-dimethylamino-1-(1-methyl-1H-indole-3-yl)-2-propen-1-one (III) can refer to a preparation method for the same compound in the literatures Tetrahedron, 63(41), 10169-10176; 2007 and Journal of Organic Chemistry, 80 (9), 4722-4728; 2015; and preparation of $N^1,N^1,N^2$-trimethyl-1,2-ethylenediamine can refer to a preparation method for the same compound in the literatures Journal of Medicinal Chemistry, 35(1), 38-47; 1992 and Journal of Materials Chemistry B: Materials for Biology and Medicines, 2(25), 3915-3918; 2014.

Example 1

2-fluoro-4-methoxyaniline (IV) (14.1 g, 0.1 mol), triethylamine (12 g, 0.12 mol) and dichloromethane 150 mL were added in a reaction bottle, and were cooled to a temperature of 0-5° C. by ice bath, acryloyl chloride (13.6 g, 0.15 mol) was dropwise added during stirring, and after dropwise adding was finished, heating to room temperature was carried out, and reaction was continued for 3-5 hours to finish TLC detection reaction. 10 mL of methanol was added for quenching reaction, and reaction liquid was washed with 100 mL of a saturated sodium bicarbonate solution, and was dried with anhydrous sodium sulfate. A solvent was recycled under reduced pressure, residues were recrystallized with n-hexane, and were dried under vacuum to obtain white solid N-(2-fluoro-4-methoxy)phenyl-2-propenamide (V) 15.9 g, and the yield was 81.5%; and EI-MS m/z: 196 $[M+H]^+$.

Example 2

N-(2-fluoro-4-methoxy)phenyl-2-propenamide (V) (9.75 g, 0.05 mol), $N^1,N^1,N^2$-trimethyl-1,2-ethylenediamine (6.12 g, 0.06 mol) and N,N-dimethylacetamide (100 mL) were added in a reaction bottle, diisopropylethylamine (10.1 g, 0.08 mol) as an alkali accelerator was dropwise added at room temperature, and after dropwise adding was finished, heating to a temperature of 85-95° C. was carried out, and reaction was continued for 3-5 hours to finish TLC detection reaction. Cooling was carried out, 50 mL of water was added, stirring and crystallizing was carried out, a filter cake was washed with cold water, and was dried to obtain faintly yellow solid N-[2-[[2-(dimethylamino)ethyl]methylamino]-4-methoxy]]phenyl-2-propenamide (VI) 12.0 g, and the yield was 86.6%; and EI-MS m/z: 278 $[M+H]^+$.

Example 3

Under cooling by ice bath, N-[2-[[2-(dimethylamino) ethyl]methylamino]-4-methoxy]]phenyl-2-propenamide (VI) (6.9 g, 25 mmol) and 20 mL of sulfuric acid with the mass concentration of 98% were added in a reaction bottle, and a temperature of a system was maintained at 5-10° C. Stirring was carried out until all solid was dissolved, potassium nitrate (2.5 g, 25 mmol) was added in batches, and after adding was finished, the reaction fluid was heating to room temperature was carried out, and stirring reaction was carried out for 12 hours to finish TLC detection reaction. Reaction fluid was poured into 100 mL of ice water, and was extracted with dichloromethane for three times, organic phases were merged, were washed with a saturated sodium bicarbonate solution, were dried with anhydrous magnesium sulfate, were concentrated under reduced pressure, and were recrystallized with ethyl acetate and n-hexane (1:2) to obtain orange-yellow solid N-[2-[[2-(dimethylamino)ethyl]methylamino]-4-methoxy-5-nitro]phenyl-2-propenamide (VII) 5.9 g, the yield was 73.1%, and EI-MS m/z: 323 $[M+H]^+$, $^1$H NMR (DMSO-$d_6$) δ2.15 (s, 6H), 2.46 (t, 2H), 2.85 (s, 3H), 3.25 (t, 2H), 3.94 (s, 3H), 5.70 (dd, 1H), 6.22 (dd, 1H), 6.40 (dd, 1H), 7.01 (s, 1H), 7.06 (d, 1H) and 7.36 (d, 1H).

Example 4

N-[2-[[2-(dimethylamino)ethyl]methylamino]-4-methoxy-5-nitro]phenyl-2-propenamide (VII) (3.2 g, 10 mmol), ferric trichloride (0.27 g, 1 mmol), activated carbon 0.4 g and ethanol 50 mL were added in a reaction bottle, 80% hydrazine hydrate (1.25 g, 20 mmol) was dropwise added at room temperature, after adding was finished, heating to a temperature of 50-60° C. was carried out, reaction was carried out for 3-4 hours, filtering and concentrating were carried out to remove ethanol, residues were recrystallized with isopropyl ether to obtain N-[2-[[2-(dimethylamino)ethyl]methylamino]-4-methoxy-5-amino]phenyl-2-propenamide (VIII) 2.5 g, and the yield was 85.6%; and mass spectrum (EI): EI-MS m/z: 293 $[M+H]^+$, $^1$H NMR (DMSO-$d_6$) δ2.17 (s, 6H), 2.38 (t, 2H), 2.66 (s, 3H), 2.92 (t, 2H), 3.90 (s, 3H), 4.58 (brs, 2H), 5.71 (dd, 1H), 6.23 (dd, 1H), 6.41 (dd, 1H), 6.99 (s, 1H), 7.03 (d, 1H) and 7.45 (d, 1H).

Example 5

N-[2-[[2-(dimethylamino)ethyl]methylamino]-4-methoxy-5-nitro]phenyl-2-propenamide (VII) (3.2 g, 10 mmol), 10% palladium on carbon (0.16 g, 5% w/w) and ethanol 100 Ml were added in a hydrogenation reactor, hydrogen was fed into the hydrogenation reactor at room temperature under normal pressure, and reaction was carried out for 24-36 hours until the hydrogen was not absorbed any more. Filtering was carried out, a catalyst was recycled, concentrating was carried out to remove the ethanol, residues were recrystallized with isopropyl ether to obtain N-[2-[[2-(dimethylamino)ethyl]methylamino]-4-methoxy-5-amino]phenyl-2-propenamide (VIII) 2.65 g, and the yield was 90.8%; and mass spectrum (EI): EI-MS m/z: 293 $[M+H]^+$, $^1$H NMR (DMSO-$d_6$) δ2.17 (s, 6H), 2.38 (t, 2H), 2.66 (s, 3H), 2.92 (t, 2H), 3.90 (s, 3H), 4.58 (brs, 2H), 5.71 (dd, 1H), 6.23 (dd, 1H), 6.41 (dd, 1H), 6.99 (dd, 1H), 7.03 (d, 1H) and 7.45 (d, 1H).

Example 6

N-[2-[[2-(dimethylamino)ethyl]methylamino]-4-methoxy-5-amino]phenyl-2-propenamide (VIII) (2.9 g, 10 mmol), a hydrogen cyanamide aqueous solution (1.7 g, 20 mmol) with the mass concentration of 50% and n-butanol 50 mL were added in a reaction bottle, and were heated to a temperature of 80-90° C., 1.5 mL of concentrated hydrochloric acid with the mass concentration of 36% was added, stirring reaction was carried out for 2 hours, then 1.5 mL of the concentrated hydrochloric acid with the mass concentration of 36% was added, and reaction was continued for 6-8 hours by keeping the temperature to finish TLC detection reaction. Cooling was carried out so that solid was separated out, the solid was filtered, a filter cake was washed with cold n-butanol to obtain yellowish-brown solid N-[2-[[2-(dimethylamino)ethyl]methylamino]-4-methoxy-5-formamidine]phenyl-2-propenamide (II) 2.2 g, and the yield was 65.7%; EI-MS m/z: 335 $[M+1-1]^+$, $^1$H NMR (DMSO-$d_6$) δ2.23 (s, 6H), 2.37 (t, 2H), 2.67 (s, 3H), 2.92 (t, 2H), 3.91 (s, 3H), 5.70 (dd, 1H), 6.22 (dd, 1H), 6.40 (dd, 1H), 7.10 (d, 1H), 7.45 (m, 1H) and 7.52 (m, 1H).

Example 7

N-[2-[[2-(dimethylamino)ethyl]methylamino]-4-methoxy-5-formamidine]phenyl-2-propenamide (II) (1.7 g, 5 mmol), (2E)-3-dimethylamino-1-(1-methyl-1H-indole-3-yl)-2-propen-1-one (III) (1.2 g, 5.3 mmol), sodium hydroxide (0.8 g, 10 mmol) and n-butanol 35 mL were added in a reaction bottle, were heated to a temperature of 90-105° C.

step by step, and were subjected to stirring reaction for 24-30 hours to finish TLC detection reaction. Cooling and crystallizing were carried out, an obtained filter cake was recrystallized with ethanol/ethyl acetate (1:1), and was dried under vacuum to obtain yellow solid AZD9291 (I) 4.55 g, and the yield was 91.0%; and EI-MS m/z: 500 [M+H]$^+$, $^1$H NMR (DMSO-d6) δ2.21 (s, 6H), 2.29 (t, 2H), 2.72 (s, 3H), 2.89 (t, 2H), 3.86 (s, 3H), 3.92 (s, 3H), 5.77 (dd, 1H), 6.27 (dd, 1H), 6.43 (dd, 1H), 7.04 (s, 1H), 7.15 (t, 1H), 7.24 (m, 2H), 7.53 (d, 1H), 7.91 (s, 1H), 8.24 (d, 1H), 8.33 (d, 1H), 8.68 (s, 1H), 9.14 (s, 1H) and 10.22 (s, 1H).

It should be noted that the examples discussed above are merely for describing the technical concept and features of the invention, their objective is that those skilled in the art could understand the content of the invention and implement therefrom, and limitation to the scope of protection of the invention cannot be made only by these examples. All equivalent changes or modifications according to the spirit of the invention should fall within the scope of protection of the invention.

What is claimed is:

1. A compound N-[2-[[2-(dimethylamino)ethyl]methylamino]-4-methoxy-5-formamidine]phenyl-2-propenamide as shown in formula II

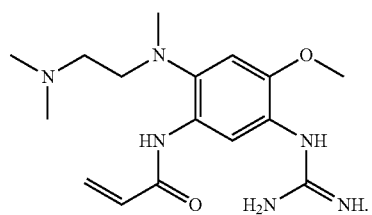

II

2. A preparation method of the compound according to claim 1 comprising:
preparing N-(2-fluoro-4-methoxy)phenyl-2-propenamide by reacting 2-fluoro-4-methoxyphenylamine and acryloyl chloride in the presence of an acid-binding agent selected from the group consisting of triethylamine, sodium bicarbonate, potassium carbonate, lithium carbonate, cesium carbonate, potassium tert-butoxide, and sodium tert-butoxide;
preparing N-[2-[[2-(dimethylamino)ethyl]methylamino]-4-methoxy]]phenyl-2-propenamide by reacting (2-fluoro-4-methoxy)phenyl-2-propenamide and N$^1$,N$^1$,N$^2$-trimethyl-1,2-ethylenediamine in the presence of an alkali accelerator selected from the group consisting of triethylamine, pyridine, N-methylmorpholine, diisopropylethylamine, 4-dimethylaminopyridine, triethylene diamine, 1,8-diazabicycloundec-7-ene, and tetramethylethylenediamine;
preparing N-[2-[[2-(dimethylamino)ethyl]methylamino]-4-methoxy-5-nitro]phenyl-2-propenamide by a nitrification reaction of N-[2-[[2-(dimethylamino)ethyl]methylamino]-4-methoxy]phenyl-2-propenamide;
preparing N-[2-[[2-(dimethylamino)ethyl]methylamino]-4-methoxy-5-amino]phenyl-2-propenamide by a nitro reduction reaction of N-[2[[2-(dimethylamino)ethyl]methylamino]-4-methoxy-5-nitro]phenyl-2-propenamide, and
preparing N-[2-[[2-(dimethylamino)ethyl]methylamino]-4-methoxy-5-formamidine]phenyl-2-propenamide by a guanidination reaction of N-[2[[2-(dimethylamino)ethyl]methylamino]-4-methoxy-5-amino]phenyl-2-propenamide.

3. The preparation method according to claim 2, wherein a nitrating agent for the nitrification reaction is nitric acid or potassium nitrate.

4. The preparation method according to claim 2, wherein a reducing agent for the nitro reduction reaction is selected from the group consisting of iron, zinc, magnesium, sodium hydrosulfite, hydrazine hydrate or hydrogen; and a catalyst is ferric trichloride, activated carbon, palladium on carbon, and palladium hydroxide on carbon.

5. The preparation method according to claim 2, wherein a guanidination agent for the guanidination reaction is hydrogen cyanamide.

6. A method for preparing AZD9291 comprising reacting the compound according to claim 1 and (2E)-3-dimethylamino-1-(1-methyl-1H-indole-3-yl)-2-propen-1-one in the presence of a catalyst selected from the group consisting of sodium hydride, potassium hydride, sodium hydroxide, potassium hydroxide, sodium tert-butoxide, potassium tert-butoxide, sodium methoxide, sodium ethoxide, sodium carbonate, potassium carbonate, and cesium carbonate

AZD9291

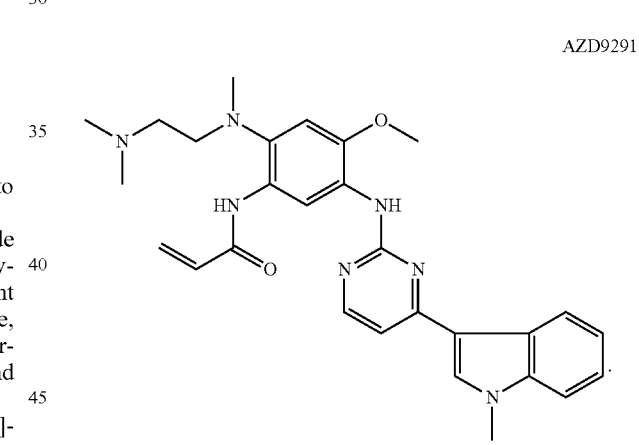

7. The method according to claim 6, wherein a molar ratio of N-[2-[[2-(dimethylamino)ethyl]methylamino]-4-methoxy-5-formamidine]phenyl-2-propenamide and (2E)-3-dimethylamino-1-(1-methyl-1H-indole-3-yl)-2-propen-1-one is 1:0.5 to 1:1.5.

8. The method according to claim 6, wherein:
a temperature of the reaction is 50-150° C.; and
a solvent for the reaction is selected from the group consisting of methylbenzene, dimethylbenzene, N,N-dimethylformamide, N,N-dimethylacetamide, n-butanol, isobutanol, and tert-butyl alcohol.

* * * * *